United States Patent [19]
Cheng et al.

[11] Patent Number: 5,616,749
[45] Date of Patent: Apr. 1, 1997

[54] PREPARATION OF LAYERED ZIRCONIUM PHOSPHITE SULFOPHENYLPHOSPHONATES AND THEIR USE AS A CATALYST

[75] Inventors: Soofin Cheng; Ren-Jai Shih, both of Taipei, Taiwan

[73] Assignee: National Science Council, Taipei, Taiwan

[21] Appl. No.: 312,884

[22] Filed: Sep. 27, 1994

[51] Int. Cl.⁶ ............................... C07F 7/00; B01J 27/18
[52] U.S. Cl. ........................ 556/13; 556/19; 556/24; 502/162
[58] Field of Search ................. 556/13, 19, 24; 502/162

[56] References Cited

U.S. PATENT DOCUMENTS

| | | | |
|---|---|---|---|
| 5,057,618 | 10/1991 | Herrmann et al. | 556/13 X |
| 5,412,128 | 5/1995 | Imuta et al. | 556/13 X |

OTHER PUBLICATIONS

S. Cheng, J.-T. Wang and C.-L. Lin, "Layered Group (IV) Metal Phosphates as Catalysts for MTBE Synthesis", Journal of the Chinese Chemical Society, 1991, 38, 529–534.

T. D. Wang and A. Clearfield, "Preparation of layered zirconium phosphonate/phosphate, zirconium phosphonate/phosphite and related compounds", Materials Chemistry and Physics, 35(1993) 208–216.

B.-Z. Wan and S. Cheng, "Nature of Zirconium Phosphite as an Acidic Catalyst", J. Chem. Soc. Faraday Trans., 1991, 87(9) 1419–1424.

S. Yamanaka, "Synthesis and Characterization of the Organic Derivatives of Zirconium Phosphate", Inorganic Chemistry, vol 15, No. 11, 1976.

G. Alberti, U. Costantino, S. Allulli and N. Tomassini, "Crystalline Zr(R-PO3)2 and Zr(R-OPO3)2 Compunds (R=Organic Radical): A New Class of Materials Having Layered Structure of the Zirconium Phosphate Type", J. inorg. nucl. Chem. vol. 40, pp. 1113–1117 (1978).

G. Alberti and U. Costantino, "Recent Progress in the Intercalation Chemistry of Layered α-Zirconium Phosphate and Its Derivatives, and Future Perspectives for Their Use in Catalysis", Journal of Molecular Catalysis, 27 (1984) 235–250.

P. M. DiGiacomo and M. B. Dines, "Lamellar Zirconium Phosphonates Containing Pendant Sulphonic Acid Groups", Polyhedron vol. 1, No. 1, pp. 31–68, 1982.

C.-Y. Yang and A. Clearfield, "The Preparation and Ion-–Exchange Properties of Zirconium Sulphophosphonates", Reactive Polymer, 5 (1987) 13–21.

*Primary Examiner*—Paul F. Shaver
*Attorney, Agent, or Firm*—Hitt Chwang & Gaines, P.C.

[57] ABSTRACT

The present invention provides zirconium phosphite sulfophenylphosphonates having the following formula $$Zr(HPO_3)_m(HPO_4)_n(PO_3C_6H_5)_y(PO_3C_6H_4SO_3H)_z$$

wherein m+n=x; x+y+z=2; 0.4≦x≦1.7; 0≦y≦1.6; and 0.01≦z≦0.8. The present invention also discloses a method of preparing these zirconium phosphite sulfophenylphosphonates and their use as a catalyst.

10 Claims, 10 Drawing Sheets

5,616,749

PREPARATION OF LAYERED ZIRCONIUM PHOSPHITE SULFOPHENYLPHOSPHONATES AND THEIR USE AS A CATALYST

FIELD OF THE INVENTION

The present invention relates to layered zirconium phosphates, in particular to layered sulfophenylphosphonic acid derivatives of zirconium phosphites.

BACKGROUND OF THE INVENTION

1. Applications of solid acid catalysts

Acid catalysts are widely used in many chemical processes, such as dehydration of alcohol, isomerization of olefin, isomerization of paraffin, alkylation, cracking, and polymerization etc. Different processes require different acidities of the acid catalysts. For example, in the reaction of producing an olefin by dehydration of an alcohol, a double bound isomerization product will be obtained if a weak acid catalyst is used in the reaction, and it takes a strong acid catalyst to obtain an olefin product with skeletal rearrangement, or an oligomer product of the olefin if the olefin formed has a high reactivity. In addition to attacking the double bound of the olefin, a strong acid catalyst also initiates a hydrogen transfer reaction and thus causes a conjunct polymerization of the olefin. Moreover, a strong acid catalyst can cause a saturated hydrocarbon undergo skeletal isomerization and alkylation. Even the most stable paraffin such as methane and ethane can be catalyzed to form a higher molecular weight hydrocarbon with a super strong acid catalyst. Some of the reactions which can be catalyzed by an acid catalyst have to be carried out at a relatively low temperature due to thermodynamic factors. For a reaction undergoing at a relatively low temperature, an strong acid catalyst having an acidity which approximates to 100% sulfuric acid is required. Sulfuric acid, hydrofluoric acid and phosphoric acid are thus often used in these reactions. However, using a liquid type acid catalyst generally involves problems such as corrosion of reactors and pipelines, and environmental pollution, etc. Therefore, there is always a need in the chemical industry to develop solid acid catalysts having strong acidity.

The acidity of a solid acid catalyst is expressed by Hammet acidity function, Ho, which is about equivalent to the pKa constant of the indicator compound. Solid acid catalysts have been extensively used in oil refinery and petrochemical industries in recent years, such as in the alkylation, isomerization, cracking and polymerization reactions. In general, most of the reactions via a reaction mechanism involving an intermediate of carbonation can be catalyzed by a solid acid catalyst. Among the common solid acid catalysts, various zeolites constructed by a matrix of silica and alumina are considered having good catalytic activities to many manufacturing processes in the oil refinery and petrochemical industries. The acidity of zeolite can reach a Ho value of −8.2, which is equivalent to 90% sulfuric acid. However, this acidity is still not strong enough to catalyze some reactions which have to be carried out at lower temperatures.

2. Synthesis of methyl tertiary butyl ether (MTBE):

Ethers, such as Methyl Tertiary Butyl Ether (MTBE), Ethyl Tertiary Butyl Ether (ETBE) and Methyl Tertiary Amyl Ether (TAME), are introduced into gasoline as octane boosting additives, because these ethers have high octane number ({RON+MONumber}/2 higher than 105), high combustion value, low water solubility (lower than 4.8%), low volatility (RVP=8 psi), and they are fully miscible with gasoline and less toxic. These ethers not only can make up the octane number lost by the reduced lead content of the unleaded gasoline, but reduce the amount of CO, NO and hydrocarbon compounds generated by the incomplete combustion of the gasoline due to oxygen contained therein. Among these ethers, MTBE is the most popular one due to its low price.

In 1907 Belgium chemist, Reychler first synthesized a tertiary ether by mixing trimethyl ethene, methanol and sulfuric acid [Reychler, Buul. Soc. Chim. Belg., 21 (1907) 71]. Up to the present, MTBE is synthesized similarly by reacting methanol and isobutene in the presence of an acid catalyst, wherein the acid catalyst used mostly is a Brönsted type solid acid catalyst except that $BF_3$ [H. G. Shnelder and N. J. Roselle, U.S. Pat. No. 2,197,023.] and Pt salts [U.S. Pat. No. 3,718,701.] are Lewis acid. In the literature, the solid acid catalysts which have been used for synthesizing MTBE includes: Zeolite {H-ZSM, ZSM-11, mordenite [P. Chu, G. T. Kuhl, Ind. Eng. Chem. Res. 26 (1987) 365.; L. M. Tan and B. H. Davis, Appl. Catal., 53 (1989) 263.; and S. I. Pien and W. J. Hatcher, Chem. Eng. Comm., 93 (1990) 257.]}, montmorillonite [J. M. Adams, K. Martin, R. W. McCabe and S. Murray, Clays & Clay Miner., 34 (1986) 597. M. P. Atkins, J. Williams, J. A. Ballantine, J. H. Purnell, Eur. Pat. Appl. EP 284397 A1 (1988)], acidic $TiO_2$[J. K. Knifton and N. J. Grice, U.S. U.S. Pat. No. 4,822,921], acidic alumina [F. Ancilloti, M. M. Mauri, E. Pescarollo and I. Romagnoni, J. Mol. Catal. 4 (1978) 37.], Kieselguhr [U.S. Pat. No. 3,906,054], heteropoly acid salt (HPA salt) [J. S. Kim, G. Seo, N. C. Park and H. Niiyama, Appl. Catal. 37 (1988) 45.], HPA/$TiO_2$ [J. F. Knifton, U.S. Pat. No. 4,827, 048 A (1989)], FCSA (supported fluorocarbon sulfonic acid polymer) [L. M. Tan and B. H. Davis, Appl. Catal., 53 (1989) 263.; and J. D. Weaver, E. I. Tasset and W. E. Fry in "Catalysis 1987—Studies in Surface Science and Catalysis, Vol. 38" J. W. Ward ed., Elsevier, Amsterdam, p. 24, 1988.,14], PPA (a phenylphosphonic acid resin) [D. E. Pearson, U.S. Pat. No. 4,133,838 (1979).], Nafion-H [F. J. Waller and R. W. van Scoyoc, Chemtech, July (1987) 438.] and a sulfonic acid type resin Amberlyst-15 (A-15) [A. Ali and S. Bhtia, Chem. Eng. J., 44 (1990) 97.], etc. Among them, A-15 is currently used in the chemical industry for manufacturing MTBE.

Amberlyst-15 resin is a macroreticular cation-exchanger and a sulfonic acid type based on a styrene-divinylbenzene copolymer. The catalyst was reported to be unstable above 90%, and overheating caused release of sulfonic and sulfuric acids [N. W. Frish, Chem. Eng. Sci. 17 (1962) 735.]. A-15 even used in a lower temperature reaction will release a small amount of acidic material to the reaction products [S. Yamanaka and M. Koizunii, Clays & Clay Miner. 23 (1975) 477.], which may in turn cause the engine corrosive.

3. Development of zirconium phosphate derivatives:

The research related to layered metal (IV) phosphate compounds and the derivatives thereof was started from 1964. In that year, Clearfield and Stynes first synthesized zirconium phosphate crystal, identified the synthesized compound as $Zr(HPO_4)_2 \cdot H_2O$ and presented the matrix structure of the crystal [A. Clearfield and J. A. Stynes, J. Inorg. Nucl. Chem., 26 (1964) 117].

In 1970's Yamanaka [S. Yamanaka, Inorg. Chem. 15 (1976) 2811.] and Alberti et al. [G. Alberti, V. Costantino and N. Tomassini, J. Inorg. Nucl. Chem. 40 (1978) 1113.] synthesized a layered zirconium phosphate having a bridge-bonded organo substituent with a general formula of Zr(PO₃R)₂, such as $Zr(PO_3C_6H_5)_2$. This compound is significant in: (i) a relatively low synthesizing temperature unlike the previous solid compounds which can only be synthesized at a high temperature, (ii) a structure similar to that of zirconium phosphate, i.e. the organo substituent being bridged-bonded the same way as the phosphate bond. These properties allow us to design various layered zirconium phosphates with different substituents above and below the zirconium plane thereof, e.g. $Zr(RPO_3)_x(R'PO_3)_{2-x}$, wherein R and R' are an organo substituent, H, OH or OR; and 0<x<2 [G. Alberti and U. Costrantina, J. Mol. Catal. 27 (1984) 235.]. Occidental Research Corporation in the European Patent Application No. 10,857 [P. M. DiGiacomo, M. B. Dines and V. E. Parziale, European Patent Appl. 0 010 857 A2 (1979).] claims a layered or amorphous organometallic inorganic polymer of the formula: $M(O_3ZO_xR)_n$, wherein M is at least one tetravalent metal; Z is a pentavalent metal; R is one or more organo groups; and n is 2. Compound $Zr(O_3PC_6H_4SO_3H)_2$ is also covered by this broad claim; however, it was not synthesized in the specification. As a matter of fact, it cannot be synthesized in accordance with the solution synthesis method disclosed in the specification due to its high solubility in water.

DiGiacomo and Dines in 1982 reported a method of synthesizing a zirconium phosphate sulfophenylethylenephosphonate, $Zr(O_3PC_2H_4C_6H_4SO_3H)_2$, by using a corrosive HF acid, wherein the product obtained was non-crystalline and unstable [P. M. DiGiacomo and M. B. Dines, Polyhedron 1 (1982) 61]. In 1987, Yang and Clearfield utilized a similar method to synthesize a zirconium sulfophenylphosphonate having a phosphite group and an interlayer spacing of 16.1Å [C. Y. Yang and A. Clearfield, React. Polym. 5 (1987) 13], which includes the following steps: dissolving a small amount of $ZrOCl_2 \cdot 8H_2O$ in an aqueous HF acid solution to form zirconium fluoro complex; adding phosphorous acid and phenylphosphonic acid to the mixture while vigorously stirring; keeping the mixture in 60° C. water bath for 3 days; removing the precipitate from the mixture and sulfonating the precipitate with oleum. Although this method can produce a zirconium sulfophenylphosphonate with a high crystallinity, it is only suitable to small scale production. In addition, a corrosive HF acid is used.

In 1990, Clerici et al. disclosed a replacement method to obtain zirconium phosphate sulfophenylphosphonate deposited on silica, which comprises depositing α-zirconium phosphate on silica; immersing the deposited silica in a sealed bottle together with sulfophenylphosphonic acid at a temperature of 80° C. for 20 days [M. G. Clerici, G. Alberti, M. Malentacchi, G. Bellussi, A. Prevedello and C. Corno, Eur. Pat. Appl. 0 386 845 A1 (1990)]. The replacement method has a problem in controlling the composition of the product.

One of the present inventors, Soofin CHENG, and her co-workers in an article, entitled "Layered Group(IV) Metal Phosphates as Catalysts for MTBE Synthesis" Journal of the Chinese Chemical Society, 1991, 38, 529–534, disclose layered phenylsulfonic acid derivatives of zirconium phosphate prepared by mixing an aqueous solution of $ZrOCl_2$ with excess $H_3PO_4$ solution (1.5M). After stirring at room temperature for 12 hours, the white gel was centrifuged and washed with deionized water until free of Cl-ions. A crystalline sample was obtained by refluxing the gel in a $H_3PO_4$ solution (4.5M) for 48 hours, which was confirmed by its X-ray diffraction pattern and IR spectrum to be α-zirconium phosphate [formulated as $Zr(HPO_4)_2 \cdot H_2O$]. The phenyl phosphonate derivative was prepared by refluxing zirconium phosphate gel (25g) or α-zirconium phosphate in phenyl phosphonic acid solution (300 mL, 3M) for 2 hours, followed by washing and drying. The resultant solids were sulfonated with fuming sulfuric acid according to the procedures described by Yang and Clearfield [C. Y. Yang and A. Clearfield, React. Polym. 5 (1987) 13]. The phenylsulfonic acid derivatives of zirconium phosphate prepared by this method possess high acidity (–5.6>Ho>–8.2) and give high activity toward MTBE formation, but this method as well as the sulfonation methods mentioned above all suffer drawbacks as follows: (i) a very low yield of the layered solid product, e.g. most being lower than 50% based on Zr content, and (ii) it is very difficult in controlling the amount of sulfonic acid groups incorporated in the layered structure and thus the reproductivity is very poor.

An object of the present invention is to provide an improved method of preparing a sulfophenylphosphonate derivative of zirconium phosphite (which is also termed zirconium phosphite sulfophenylphosphonate in the text of this specification), which does not has the drawbacks of the prior art methods as mentioned above.

Another object of the present invention is to provide a method of using a sulfophenylphosphonate derivative of zirconium phosphite as an acid catalyst, in which the sulfophenylphosphonate derivative of zirconium phosphite has a catalytic activity higher than that of Amberlyst-15 (A-15) resin in MTBE synthesis reaction.

SUMMARY OF THE INVENTION

A method of preparing a zirconium phosphite sulfophenylphosphonate in accordance with the present invention comprises the following steps:

(a) reacting phenylphosphonic acid with an excess amount of fuming sulfuric acid at a temperature from about 80° C. to about 150° C. to convert substantially all the phenylphosphonic acid to sulfophenylphosphonic acid;

(b) cooling the reaction mixture to a temperature below about 80° C.

(c) mixing the cooled reaction mixture with: (i) phosphorous acid; (ii) an aqueous or organic solution of zirconium salt; and (iii) phenylphosphonic acid when y is >0, to give a resultant solution mixture;

(d) stirring the resultant solution mixture at a temperature between about 150° C. and room temperature until a co-precipitate is formed therein;

(e) removing the co-precipitate from the solution mixture; and (f) washing and drying the co-precipitate.

Preferably, the zirconium phosphite sulfophenylphosphonate prepared by the present method have the following formula

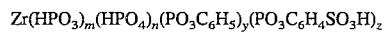

wherein m+n=x; x+y+z=2; 0.4≦x≦1.7; 0≦y≦1.6; 0.01≦z≦0.8.

It is believed that the layered crystalline product obtained by the present method contains phosphate group converted from phosphite group during the preparation steps, even though the present method does not use phosphoric acid as a reactant. A discussion of this transformation can be found in B.-Z. Wan, S. Cheng, R. G. Anthony and A. Clearfield, J. Chem. Soc. Faraday Trans., 1991 87(9), 1419–1424, the disclosure of which is incorporated herein by reference.

Zirconium phosphite sulfophenylphosphonates of various compositions can be obtained by the present method by controlling the mixing ratio of sulfophenylphosphonic acid, phosphorous acid and phenylphosphonic acid, whereby the optimal conditions for preparing the compounds with high catalytic activities and high yields can be found.

Preferably, the mixing molar ratio of zirconium (Zr): sulfophenylphosphonic acid ($H_2PO_3C_6H_4SO_3H$): phosphorous acid ($H_3PO_3$): phenylphosphonic acid ($H_2PO_3C_6H_5$) in step (c) is 1:10:a: b, wherein $6 \leq a \leq 50$; $0 \leq b \leq 10$.

Preferably, the reaction temperature in step (a) is about 120° C.

Preferably, the stirring temperature in step (c) is about 110° C.

Preferably, the cooling temperature in step (b) is room temperature.

The present invention also provides a solid acid catalyst for an acid catalyzed reaction comprising a zirconium phosphite sulfophenylphosphonate prepared by the present method. Preferably, the acid catalyzed reaction is gas phase synthesis of methyl tert-butyl ether (MTBE) from methanol and isobutene.

DETAILED DESCRIPTION OF THE INVENTION

Figure 1:
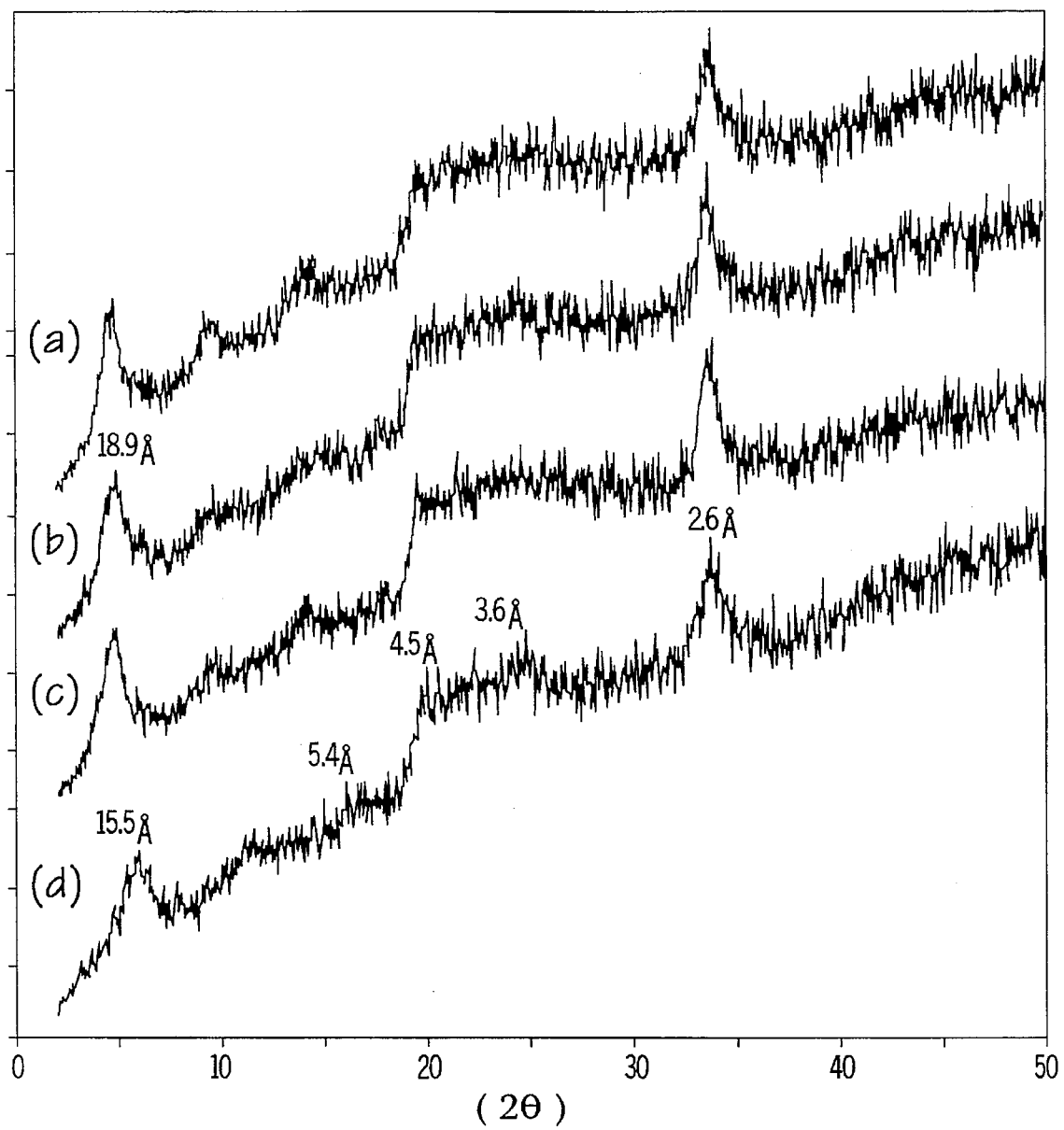
FIG. 1 shows X-ray diffraction (XRD) patterns of zirconium phosphite sulfophenylphosphonates with Zr: $H_2PO_3C_6H_4SO_3H$: $H_3PO_3$: $H_2PO_3C_6H_5$ molar ratio of 1:10:a:b which are termed as Zr(a,b)'s, wherein (a) is XRD pattern of Zr(6,0), (b) is XRD pattern of Zr(8,0), (c) is XRD pattern of Zr(10,0), and (d) is XRD pattern of Zr(8,0) dehydrated at 180° C.

1. Synthesis of zirconium phosphite sulfophenylphosphonates catalysts:

Increasing the active sites and surface area of a catalyst are two key factors for enhancing the catalytic activity of the catalyst. In the zirconium phosphite sulfophenylphosphonates synthesized by present invention, the sulfophenylphosphonate group (—$PO_3C_6H_4SO_3H$) is the main active site thereof. Pure zirconium sulfophenylphosphonate, $Zr(PO_3C_6H_4SO_3H)_2$, is supposed to have the highest catalytic activity, but it cannot be obtained in solid form via a solution reaction due to its excellent water solubility. Even though it can be separated as a solid by the other methods, problems similar to those happening in the liquid acid catalyzed cases will be encountered. From the teaching of an article by Clearfield and Yang[C. Y. Yang and A. Clearfield, React. Polym. 5 (1987) 13.], it is known that a zirconium phosphate derivative which is not soluble in water and contains sulfophenylphosphonate group can only be prepared by incorporating phosphate group ($HOPO_3$—) or phosphite group ($HPO_3$—) into the derivative. Moreover, the present inventors believe that zirconium phenylphosphonate, $Zr(PO_3C_6H_5)_2$, can be precipitated from an aqueous solution, and thus the addition of phenylphosphonic acid in a solution reaction of synthesizing zirconium phosphite sulfophenylphosphonates will be helpful in the precipitation thereof.

The present inventors are the first ones who adopt a co-precipitation method to form zirconium phosphite sulfophenylphosphonates from a mixture of phenylphosphonic acid, fuming sulfuric acid, phosphorous acid and an zirconium salt. The present co-precipitation method is advantageous in the aspects of a higher yield, an easier synthesis process, and a better control of the co-precipitated product composition, compared to the prior art synthesis methods. A typical method of preparing a zirconium phosphite sulfophenylphosphonate in accordance with the present invention comprises the following steps:

(i) reacting phenylphosphonic acid with an excess amount of fuming sulfuric acid (oleum), preferably more than twice amount of the stoichmetric amount, at a temperature of 120° C. for four hours;

(ii) under stirring, cooling the reaction mixture to room temperature, and then adding various amounts of aqueous phosphorous acid and phenylphosphonic acid solutions to the cooled mixture;

(iii) heating the solution under stirring to a temperature of 110° C., then adding less than one half of the stoichmetric amount of an aqueous solution of zirconium salt thereto, and refluxing it for nine hours by maintaining the heating and stirring, wherein a co-precipitate is formed; and (iv) removing the co-precipitate from the slurry by centrifuge, washing the co-precipitate with deionized water until the washing liquor is free of sulfate ions, and drying the washed co-precipitate at a temperature of 60° C.

EXAMPLE 1

To a 250 ml three-necked flask equipped with a reflux condenser, stirrer, thermometer and heating mantle, there were charged 23 ml fuming sulfuric acid (Union Chemical Works, Taiwan) and 11 g of first portion of phenylphosphonic acid (Janssen Chimica, Belgium). The temperature was raised to about 120° C. with stirring to gentle reflux which was continued for about 4 hours. Under stirring, the solution was cooled to room temperature and 11.5 g of phosphorous acid (Janssen Chimica, Belgium), 1.1 g of second portion of phenylphosphonic acid and water were added to make a solution of about 110 ml in volume. As the temperature of the mixture under stirring was raised to 110° C., 2.5 g of $ZrOCl_2.8H_2O$ (Hayaashi, Japan) in 30 ml of water was added slowly. A white precipitate was immediately formed. The heating and stirring were continued for 9 hours. The slurry was cooled to room temperature and the white solid was isolated by centrifuge and washing with deionized water, which was continued until the washing liquor was free of sulfate ions. The solid product was dried in an oven set at 60%. The product prepared by this example is designated as Zr(20,1).

EXAMPLE 2

The procedures of Example 1 were repeated except that the second portion of phenylphosphonic acid was omitted in preparing the acid mixture before 2.5 g of $ZrOCl_2.8H_2O$ in 30 ml of water was added slowly. The product prepared by this example is designated as Zr(20,0).

EXAMPLE 3

The procedures of Example 2 were repeated except that the temperature of the acid mixture under stirring was raised to 60° C. instead of 110° C. before 2.5 g of $ZrOCl_2.8H_2O$ in 30 ml of water was added slowly, and was maintained at 60° C. after 2.5 g of $ZrOCl_2.8H_2O$ in 30 ml of water was added slowly. The product prepared by this example is designated as Zr(20,0)-L.

Table 1 shows the weight and yield of zirconium phosphite sulfophenylphosphonates prepared by using various molar ratios of phosphorous acid, phenylphosphonic acid and 2.5 g of $ZrOCl_2.8H_2O$ in accordance with the procedures of the above examples, in which the zirconium phosphite sulfophenylphosphonate prepared with Zr: $H_2PO_3C_6H_5$ (the first portion): $H_3PO_3$: $H_2PO_3C_6H_5$ (the second portion) molar ratio of 1:10:a:b is termed hereinafter as Zr(a,b) in view of the fact that the molar ratio of Zr and $H_2PO_3C_6H_5$ (the first portion) is fixed to 1:10. For example Zr(6,1) means the molar ratio of Zr: $H_2PO_3C_6H_5$ (the first portion): $H_3PO_3$: $H_2PO_3C_6H_5$ (the second portion) used in the reaction is 1:10:6:1. It can be clearly seen from Table 1 that the yields of most examples are higher than 50%, and the highest even reaches to 99%.

Table 2 shows the elemental analysis results of the zirconium phosphite sulfophenylphosphonates in Table 1.

TABLE 1

| Precipitate | Weight, g | Yield, Zr mol % |
|---|---|---|
| Zr (6,0) | 0.50 | 17.4 |
| Zr (6,2) | 2.11 | 73.4 |
| Zr (6,4) | 2.26 | 75.8 |
| Zr (6,7) | 2.92 | 98.8 |
| Zr (8,0) | 1.64 | 58.1 |
| Zr (8,2) | 2.21 | 76.2 |
| Zr (8,4) | 2.71 | 94.7 |
| Zr (8,7) | 2.83 | 99.1 |
| Zr (10,0) | 1.56 | 60.4 |
| Zr (10,2) | 2.15 | 81.4 |
| Zr (10,4) | 2.59 | 95.6 |
| Zr (10,7) | 2.85 | 99.0 |
| Zr (20,0) | 1.35 | 55.8 |
| Zr (20,1) | 1.40 | 55.5 |
| Zr (20,5) | 2.27 | 77.4 |
| Zr (20,10) | 2.46 | 85.2 |
| Zr (30.0) | 1.48 | 63.5 |
| Zr (40,0) | 1.50 | 66.1 |

TABLE 1-continued

| Precipitate | Weight, g | Yield, Zr mol % |
|---|---|---|
| Zr (50,0) | 1.77 | 78.3 |
| Zr (40,1) | 1.68 | 72.6 |
| Zr (20,0)-L | 1.02 | 41.6 |

TABLE 2

| Precipitate | $x^{a)}$ | $y^{a)}$ | $z^{a)}$ |
|---|---|---|---|
| Zr (6,0) | 1.24 | 0.00 | 0.76 |
| Zr (6,1) | 0.97 | 0.46 | 0.57 |
| Zr (6,2) | 0.79 | 0.88 | 0.33 |
| Zr (6,4) | 0.41 | 1.44 | 0.15 |
| Zr (6,7) | 0.34 | 1.57 | 0.09 |
| Zr (8,0) | 1.28 | 0.00 | 0.72 |
| Zr (8,2) | 0.78 | 0.86 | 0.36 |
| Zr (8,4) | 0.68 | 1.11 | 0.21 |
| Zr (8,7) | 0.55 | 1.35 | 0.10 |
| Zr (10,0) | 1.26 | 0.00 | 0.74 |
| Zr (10,1) | 0.99 | 0.44 | 0.57 |
| Zr (10,2) | 0.82 | 0.84 | 0.34 |
| Zr (10,4) | 0.66 | 1.15 | 0.19 |
| Zr (10,7) | 0.54 | 1.37 | 0.09 |
| Zr (20,0) | 1.61 | 0.00 | 0.39 |
| Zr (20,1) | 1.41 | 0.26 | 0.33 |
| Zr (20,5) | 0.72 | 1.15 | 0.13 |
| Zr (20,10) | 0.4 | 1.59 | 0.01 |
| Zr (30.0) | 1.68 | 0.00 | 0.32 |
| Zr (40,0) | 1.70 | 0.00 | 0.30 |
| Zr (50,0) | 1.69 | 0.00 | 0.31 |
| Zr (40,1) | 1.69 | 0.04 | 0.27 |
| Zr (20,0)-L | 1.58 | 0.00 | 0.42 |

$^{a)}Zr(HPO_3)_m(HPO_4)_n(PO_3C_6H_5)_y(PO_3C_6H_4SO_3H)_z$, m + n = x; the calculation of z is based on sulfur; y is obtained by dividing the moles of carbon with 6 and deducting z therefrom; and x is obtained by calculating phosphorous first and then deducting y and z therefrom.

The composition of the synthesized zirconium phosphite sulfophenylphosphonate and its effect on the structure and the catalytic activity of the products are discussed as follows:

1. The effect of the molar ratio of the reactants on the yield and composition of the synthesized product:
1-1) Products synthesized without the second portion of phenylphosphonic acid:
The data of Tables 1 and 2 indicate that the yield of the product is decreasing as the content of sulfophenylphosphonate group is increasing. Moreover, the —$HPO_3$/—$PO_3C_6H_4SO_3H$ ratio of the precipitate product is maintained at a constant about 1.7, when the $H_3PO_3/H_2PO_3C_6H_4SO_3H$ ratio used in the reaction is less than one. 1-2) Products synthesized with phenylphosphonic acid:
Zr(6,1–7), Zr(8,2–7) and Zr(10,1–7) in Table 2 show the content of phenylphosphonate group of the precipitate product is increasing, and the contents of phosphite group and sulfophenylphosphonate group are decreasing, when the amount of phenylphosphonic acid used in the reaction is increasing and the $H_3PO_3/H_2PO_3C_6H_4SO_3H$ ratio is fixed. Further, the amount of phosphorous acid used in the synthesis reaction has no significant effect on the content of sulfophenylphosphonate group and has no significant relationship with the content of phosphite group incorporated in the precipitate product.
2. XRD and IR analysis
2-1) XRD and IR analysis of products synthesized without the second portion of phenylphosphonic acid
XRD analysis:
FIG. 1 shows X-ray powder diffraction patterns of the products synthesized with different amounts of phosphorous acid, in which a d-spacing value corresponding to the diffraction peak of the lowest 2θ represents the interlayer spacing of the layered compound product. The d-spacing values of the three different compounds Zr(6,0), Zr(8,0) and Zr(10,0) dehydrated at 60° C. are about 18Å (curves (a), (b) and (c)), and the crystallinity of these three compounds is not very good in view of a wide diffraction peak. The Zr(8,0) compound further dehydrated at 180° C. under vacuum shows an interlayer spacing of 15.5Å (curve (d)) which is about 3Å shorter than those of the compounds which are not subject to a further dehydration. It is believed that the compounds without further dehydration have water incorporated in the interlayer space due to a strong water affinity of the sulfonate group thereof. The following XRD analyses are directed to the compounds without further dehydration unless otherwise specified.

Figure 2:
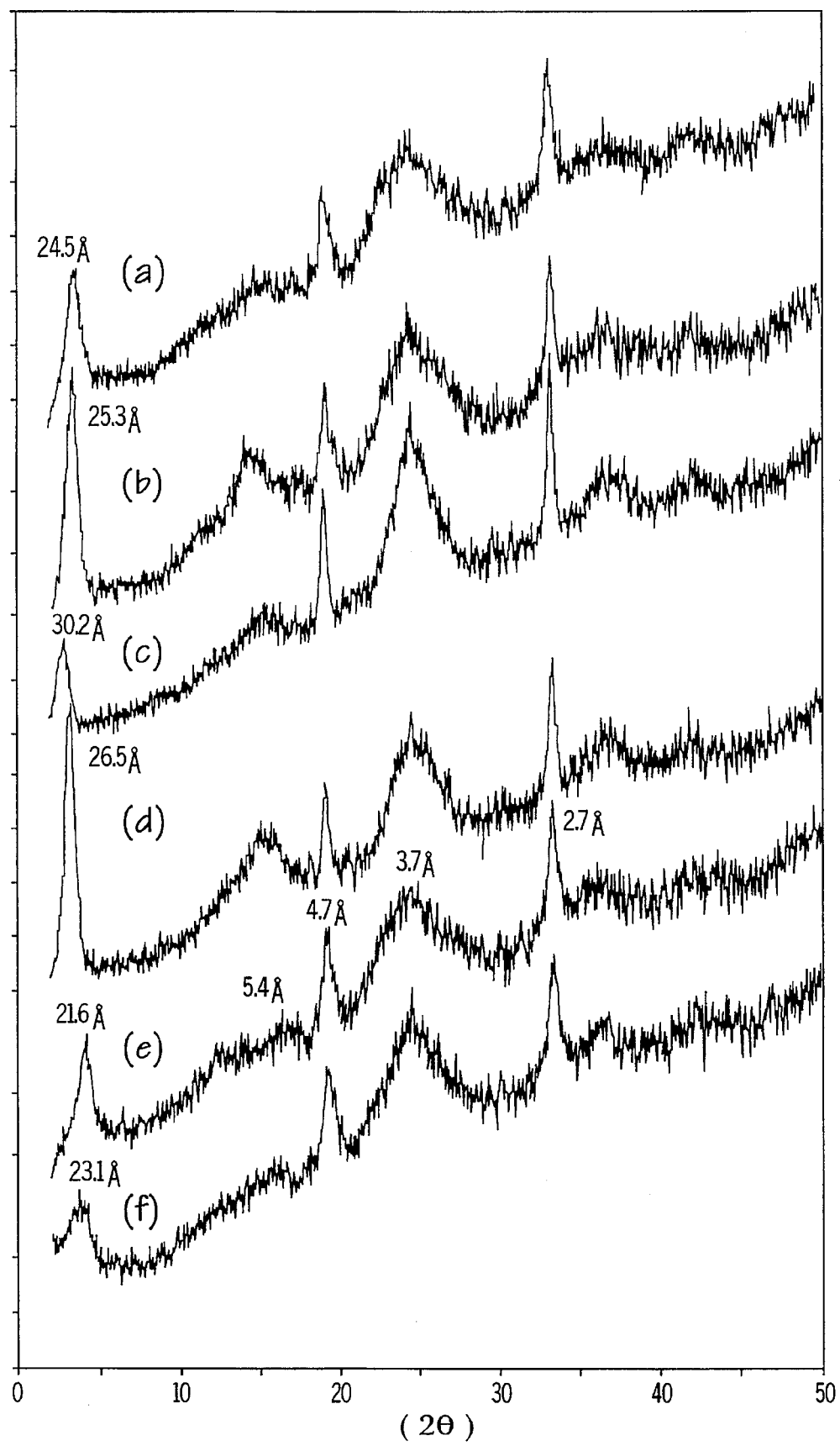
FIG. 2 shows X-ray diffraction (XRD) patterns of zirconium phosphite sulfophenylphosphonates having a higher content of phosphite group, wherein (a) is XRD pattern of Zr(20,0), (b) is XRD pattern of Zr(30,0), (c) is XRD pattern of Zr(40,0), (d) is XRD pattern of Zr(50,0), (e) is XRD pattern of Zr(20,0) dehydrated at 180° C. and (f) is XRD pattern of Zr(20,0)-L.

FIG. 2 show XRD patterns of the compounds containing a relative high amount of phosphorous acid group, the interlayer spacing values of which are about 5Å larger compared to those in FIG. 1. Curve (e) in FIG. 2 is a XRD diffraction pattern of Zr(20,0) with a further dehydration at 180° C., which shows an interlayer spacing about 21.6Å and a diffraction peak which is more steep than that of curve (d) in FIG. 1. The compounds having an interlayer spacing of about 21.6Å are considered to have segregated structures. The term "segregated product" was first mentioned by Alberti et al., React. Polym. 4 (1985) 1, for zirconium phosphite phenylphosphonate with interlayer spacing of ca. 20Å. Because zirconium phosphite has an interlayer spacing of 5.7Å, the segregated product is proposed to compose of pair of layers of 16Å and 5.7Å or that mixed with pairs of layer of ½ (16+5.7)=10.9Å. The latter is attributed to layer structure with half side of phosphite and half side of mixed phosphite and sulfophenylphosphonate. Since no peaks appeared at either 10.9Å or 16Å in the diffraction patterns, none of the corresponding phases was considered to form separately.

Figure 3:
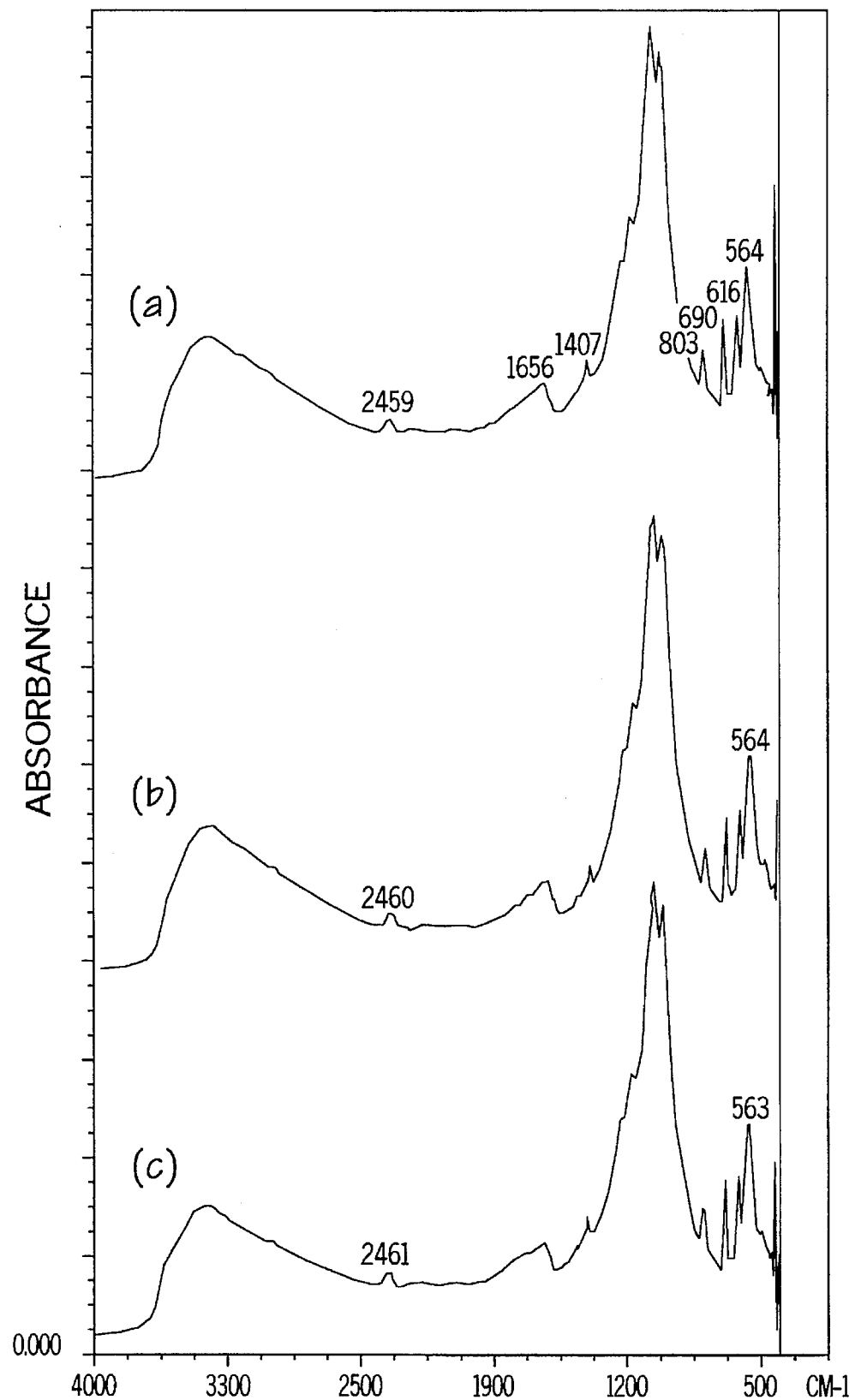
FIG. 3 shows IR spectra of zirconium phosphite sulfophenylphosphonates having a relatively low content of phosphite group, wherein a) is Zr(6,0), (b) is Zr(8,0), and (c) is Zr(10,0).
Figure 4:
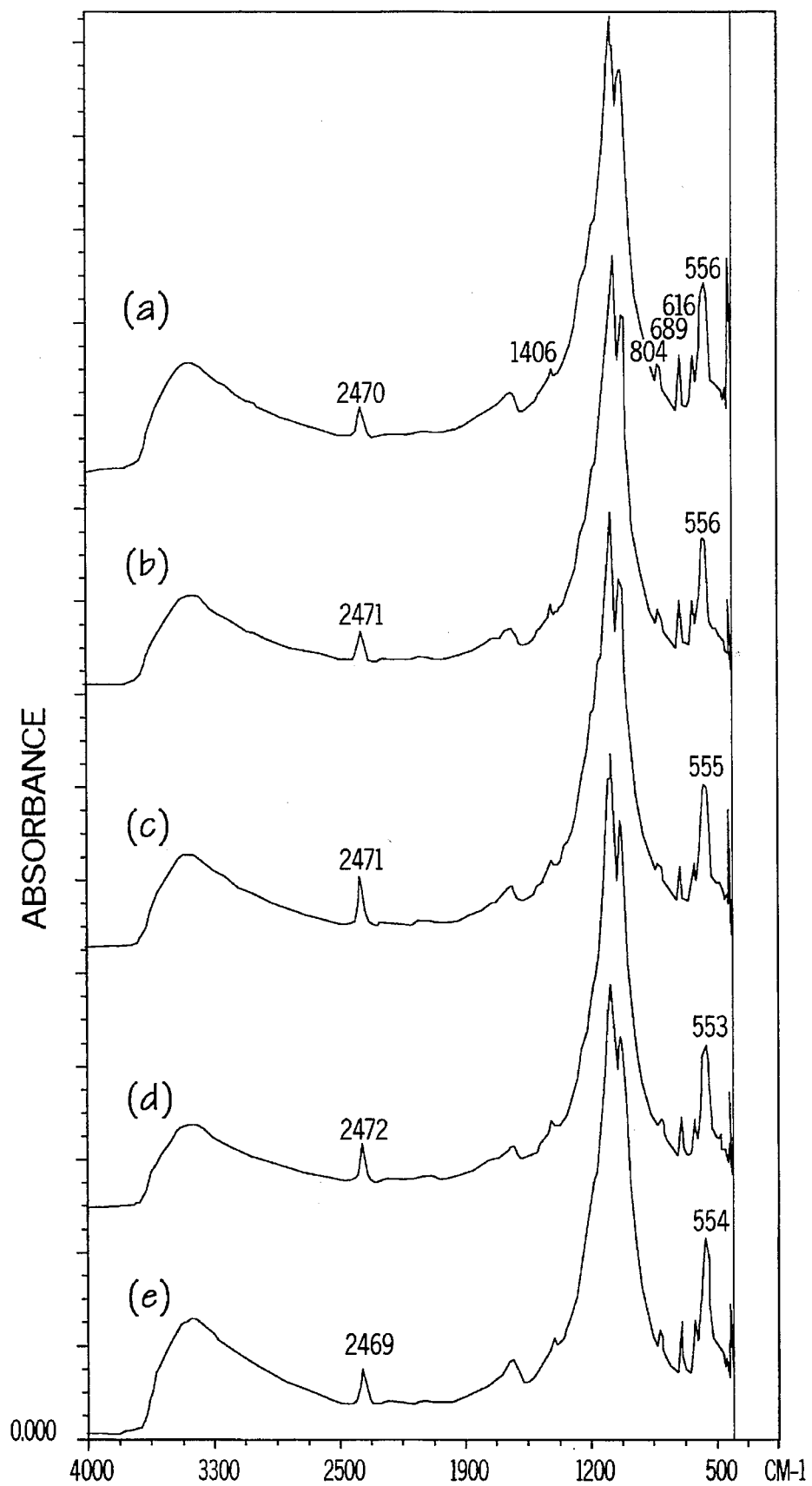
FIG. 4 shows IR spectra of zirconium phosphite sulfophenylphosphonates having a relatively high content of phosphite group, wherein (a) is Zr(20,0), (b) is Zr(30,0), (c) is Zr(40,0), (d) is Zr(50,0), and (e) is Zr(20,0)-L.

IR analysis:

FIG. 3 shows the IR spectra of compounds synthesized with a relatively small amount of phosphorous acid and having an interlayer spacing of about 18Å, such as Zr(6,0), Zr(8,0) and Zr(10,0). FIG. 4 shows the IR spectra of products synthesized with a relatively high amount of phosphorous acid and having an interlayer spacing of about 22Å, such as Zr(20,0), Zr(30,0), Zr(40,0) and Zr(50,0). The IR spectra of these compounds are all similar.

In accordance with the assignment given by Yang and Clearfield [C. Y. Yang and A. Clearfield, React. Polym. 5 (1987) 13.], the 805 $cm^{-1}$ peak corresponds to C—H out-of-plane deformation of meta di-substituted benzene ring. The 1406 $cm^{-1}$ peak corresponds to non-symmetrical stretching vibration of $SO_2$ of sulfonate group. Therefore, these absorbance peaks indicate that meta di-substituted sulfophenylphosphonic acid is formed in the reaction mixture of phenylphosphonic acid and oleum, and it is readily bounded to zirconium like $HPO_3^{2-}$. The strong absorbance peaks observed between 900–1400 $cm^{-1}$ are symmetrical and non-symmetrical vibration absorbance of $PO_3$. The vibration absorbance peak of $PO_3$ deformation appears at wavenumbers <650 $cm^{-1}$. 690 $cm^{-1}$ is an absorbance peak of P-phenyl. The absorbance peak of aromatic C—H stretching at 3050 $cm^{-1}$ does not appear and is embedded in the absorbance peak of water instead.

619 $cm^{-1}$ absorbance peak is related to sulfophenylphosphonate group, which may be a vibration absorbance peak of —$HSO_3$ deformation. 554 $cm^{-1}$ or 564 $cm^{-1}$ may be a result of overlapped vibration absorbences of various $PO_3$ deformation. The IR spectrum of pure $Zr(HPO_3)_2$ shows an intermediate-strong vibration absorbance peak of $PO_3$ deformation at 551 $cm^{-1}$, and this absorbance peak appears at 564 $cm^{-1}$ when the compounds contain a relatively small amount of phosphite group (FIG. 3), or at 554 $cm^{-1}$ when the compounds contain a relatively high amount of phosphite group (FIG. 4). Since compound containing a relatively high amount of phosphite group, such as Zr(10,0), Zr(20,0), Zr(30,0), Zr(40,0), and Zr(50,0), has a segregated layered structure with half side of phosphite, 554 $cm^{-1}$ absorbance peak appearing in FIG. 4 is very close to the 551 $cm^{-1}$ absorbance peak of $Zr(HPO_3)_2$.

Figure 5:
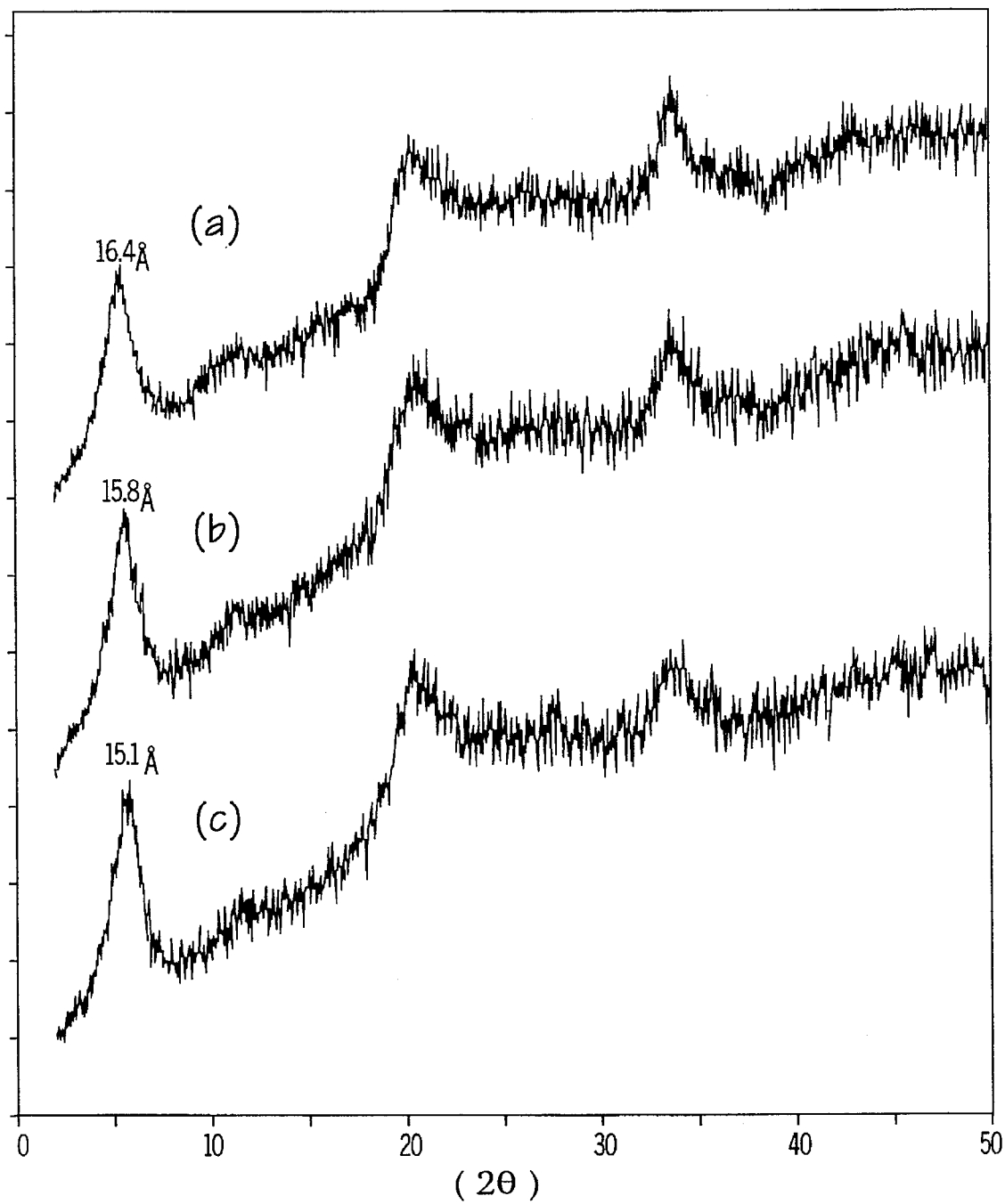
FIG. 5 shows X-ray diffraction (XRD) patterns of zirconium phosphite sulfophenylphosphonates having different contents of phenylphosphonate group, wherein (a) is Zr(6,2), (b) is Zr(6,4), and (c) is Zr(6,7).

2-2) XRD and IR analysis of products synthesized with the second portion of phenylphosphonic acid XRD analysis:

The XRD patterns of the compounds synthesized with a fixed molar ratio of Zr: sulfophenylphosphonic acid: phosphorous acid=1:10:6 and various molar ratios of phenylphosphonic acid: Zr=2, 4 and 7, i.e. Zr(6,2), Zr(6,4) and Zr(6,7), are shown in FIG. 5, from which we can see that the interlayer spacing value decreases as the amount of phenylphosphonic acid used increases. Similar XRD analyses were run for the compounds synthesized with various amounts of phosphorous acid, and the results indicated that varying the amount of phenylphosphonic acid used in the synthesis reaction has a relative strong influence on the interlayer spacing of the product than that of phosphorous acid. This observation agrees with the results of elemental analyses showing in Table 2, which demonstrates varying the amount of phenylphosphonic acid used in the synthesis reaction has a relative strong influence on the composition of the product than that of phosphorous acid.

Figure 6:
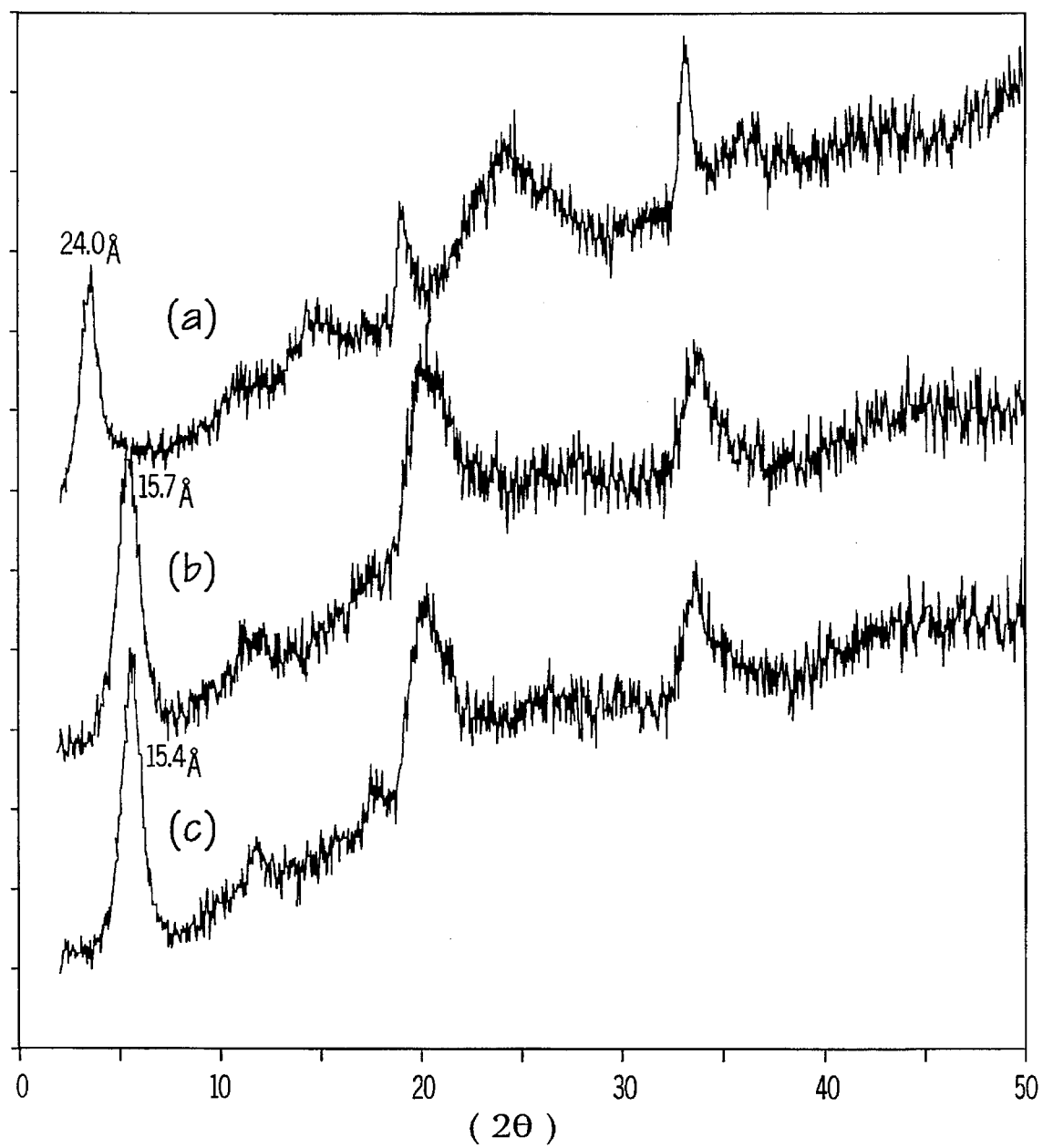
FIG. 6 shows X-ray diffraction (XRD) patterns of zirconium phosphite sulfophenylphosphonates having different contents of phenylphosphonate group, wherein (a) is Zr(20,1), (b) is Zr(20,3), and (c) is Zr(20,10).

The XRD patterns of the compounds synthesized with a fixed molar ratio of Zr: phenylphosphonic acid (the first portion): phosphorous acid=1:10:20 and various molar ratios of the second portion phenylphosphonic acid: Zr=1, 5 and 10, i.e. Zr(20,1), Zr(20,5) and Zr(20, 10), are shown in FIG. 6. The interlayer spacing of Zr(20,1) is 24Å which is similar to that of Zr(20,0), the compound synthesized with same amount of phosphorous acid but without the second portion of phenylphosphonic acid, and thus they both are segregated products.

Figure 7:
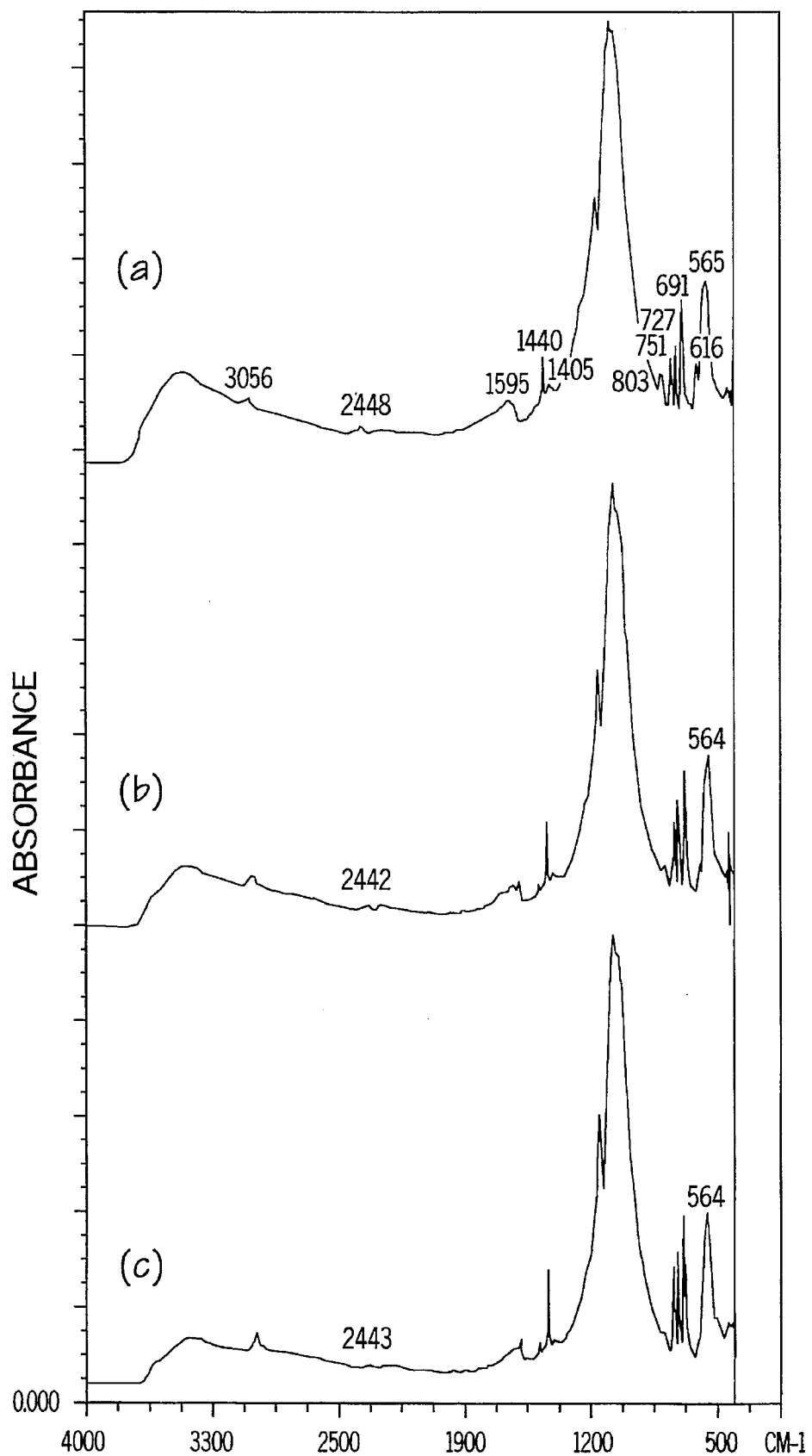
FIG. 7 shows IR spectra of zirconium phosphite sulfophenylphosphonates having different contents of phenylphosphonate group, wherein (a) is Zr(6,2), (b) is Zr(6,4), and (c) is Zr(6,7).

IR analysis:

The main difference between the compounds synthesized with and without the second portion of phenylphosphonic acid in the IR spectra is the former has an absorbance peak of mono-substituted benzene ring and the latter hasn't. FIG. 7 shows IR spectra of the compounds synthesized with various amounts of phenylphosphonic acid, each of which is observed to have absorbance peaks of 728 $cm^{-1}$ and 750 $cm^{-1}$, the absorbance peaks of out-of-plane deformation of mono-substituted benzene ring.

3. Surface analysis

Table 3 show the BET surface areas of the non-segregated products, i.e. a product having an interlayer spacing value of about 16Å. It can be found from Table 3 that the surface areas of the products Zr(6,0), Zr(8,0) and Zr(10,0) are all lower than 10 $m^2$/g. Referring to the elemental analysis data in Table 2, these three products have a molar ratio of —$PO_3H$ /—$PO_3C_6H_4SO_3H$ about 1.7, i.e. —$PO_3C_6H_4SO_3H$/(—$PO_3C_6H_4SO_3H$+—$PO_3H$)=0.35. At this ratio, the —$PO_3C_6H_4SO_3H$ will clog most of the internal pores of the products. The data of Tables 3 and 2 show that the surface area will increase as the —$PO_3C_6H_4SO_3H$ content of the product decreases. A similar phenomenon is observed when the content of —$PO_3C_6H_5$ varies. For example, the products Zr(6,7) and Zr(10,7) have —$PO_3C_6H_4SO_3H$/Zr ratios about equal to 0.09, but Zr(6,7) has a smaller surface area because it has a higher concentration of —$PO_3C_6H_5$ group. In order to increase the surface area of the present layered product, the contents of the —$PO_3C_6H_4SO_3H$ and —$PO_3C_6H_5$ groups should be kept at a lower level. However, the acidity of the —$PO_3C_6H_4SO_3H$ group is the main catalytic activity of the present layered product, the content of which cannot be reduced to a level which is detrimental to the catalytic activity thereof.

Table 4 show the surface areas of the segregated products. Among the Zr(20,0), Zr(20,1 ), Zr(30,0), Zr(40,0) and Zr(50,0) products, only Zr(20,1) contains phenylphosphonate group and has the smallest surface area. With reference to Table 2, it can be found that the surface area decreases when the content of —$PO_3C_6H_4SO_3H$ group of the product increases. For example, the surface areas of Zr(20,0), Zr(30, 0) and Zr(40,0) have a order of Zr(20,0)<Zr(30,0)<Zr(40,0).

4. Thermogravimetric analysis

Figure 8:
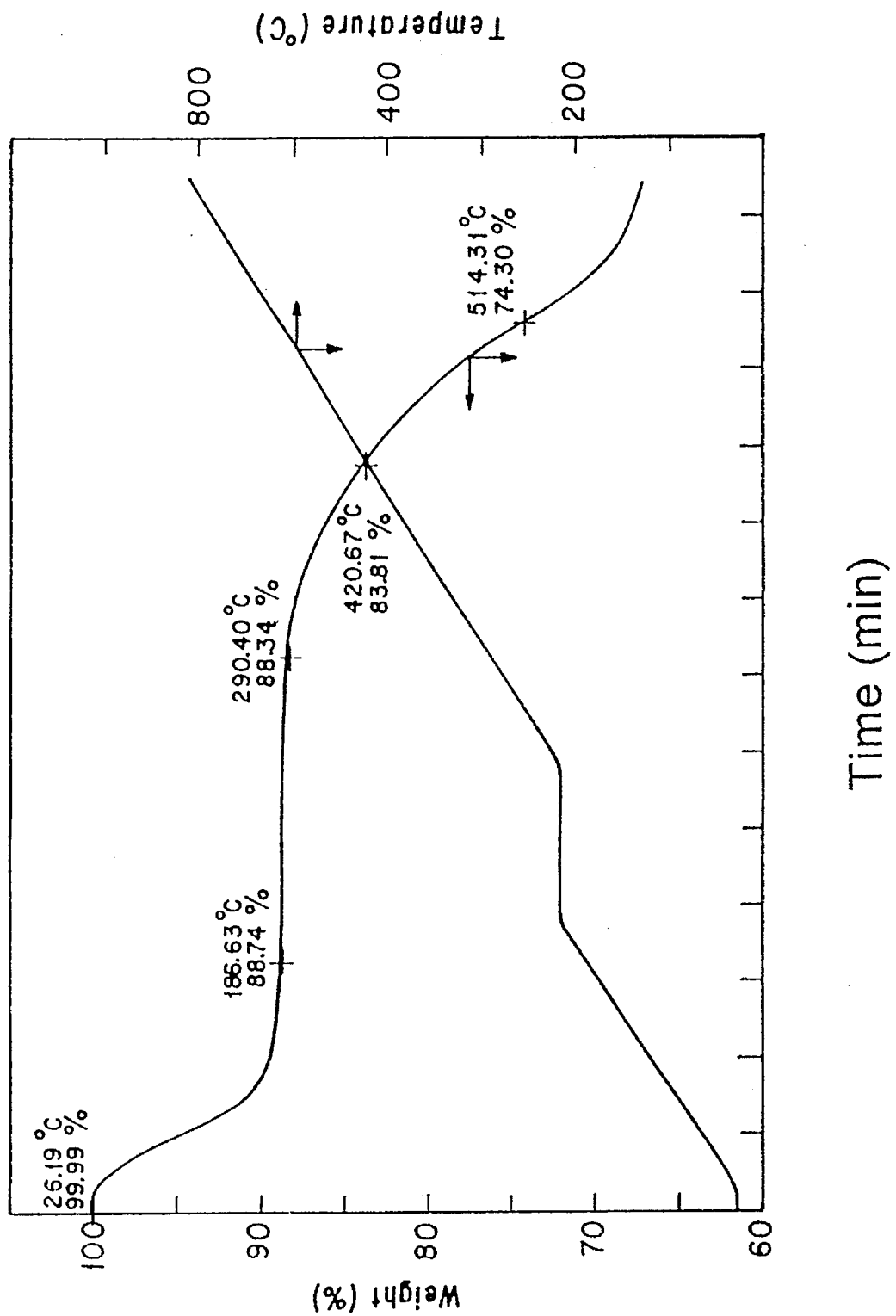
FIG. 8 is a plot which shows thermogravimetric analysis (TGA) results of Zr(8,2).
Figure 9:
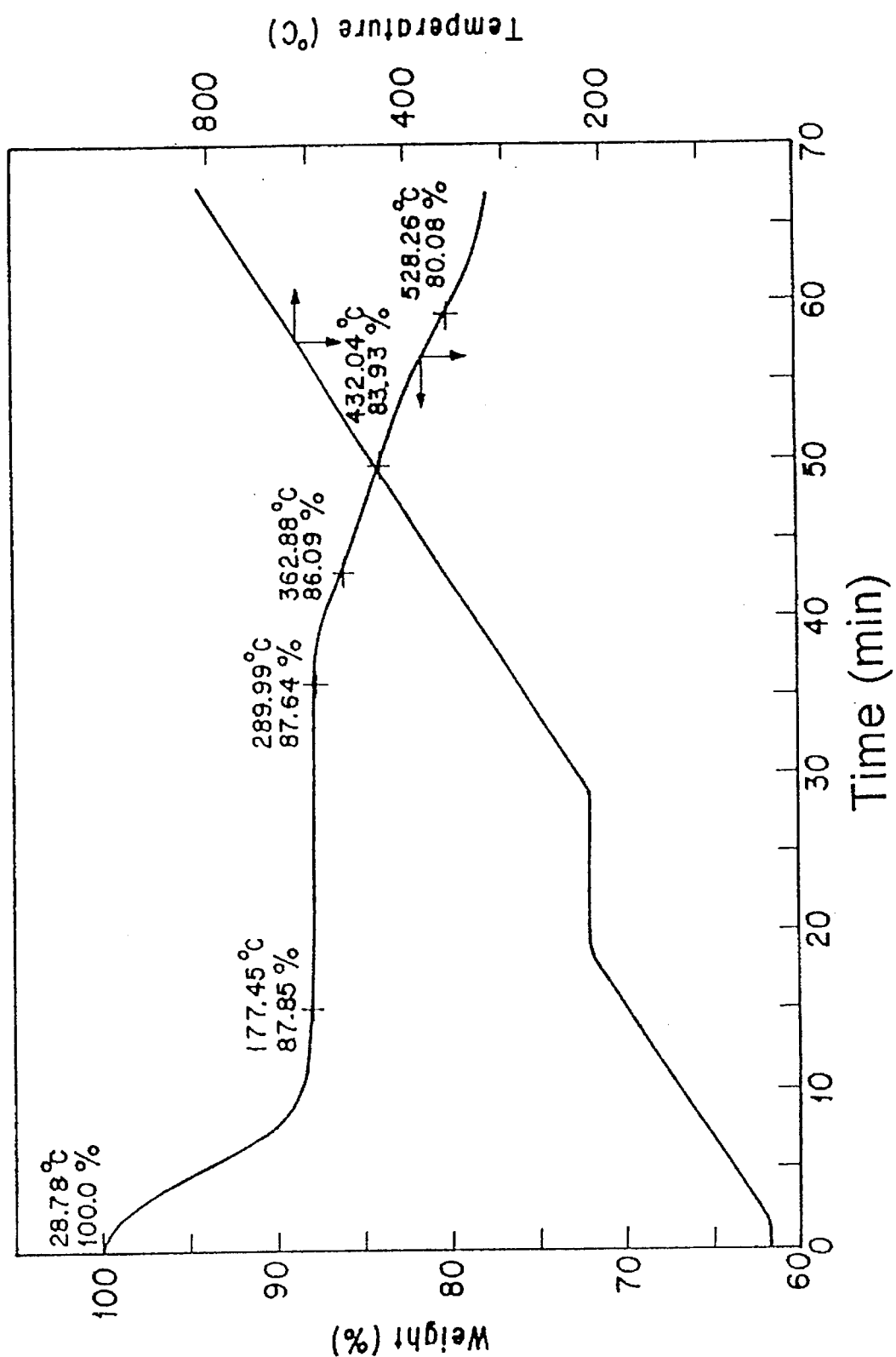
FIG. 9 is a plot which shows thermogravimetric analysis (TGA) results of Zr(20,0).

FIGS. 8 and 9 show the thermogravimetric analysis (TGA) results of the non-segregated and segregated products, respectively. The weight lost under 200° C. or lower temperatures in FIGS. 8 and 9 is water absorbed in the products, and the decomposition of the products is started at 290° C. Therefore, the layered products synthesized by the present invention can be used in a catalytical reaction taking place at a temperature lower than 290° C.

TABLE 3

| Precipitate | Surface area, $m^2/g$ |
| --- | --- |
| Zr (6,0) | 8 |
| Zr (6,1) | 10 |
| Zr (6,2) | 22 |
| Zr (6,4) | 50 |
| Zr (6,7) | 120 |
| Zr (8,0) | 5 |
| Zr (8,2) | 39 |
| Zr (8,4) | 143 |
| Zr (8,7) | 207 |
| Zr (10,0) | 3 |
| Zr (10,1) | 9 |
| Zr (10,2) | 38 |
| Zr (10,4) | 182 |
| Zr (10,7) | 229 |
| Zr (20,5) | 248 |
| Zr (20,10) | 255 |

TABLE 4

| Precipitate | Surface area, $m^2/g$ |
| --- | --- |
| Zr (20,0) | 152 |
| Zr (20,1) | 125 |
| Zr (30,0) | 162 |
| Zr (40,0) | 180 |
| Zr (50,0) | 143 |

5. The acid amount analysis

Since the product will decompose at a temperature of about 290° C., a temperature programmed desorption of $NH_3$ cannot be used to measure the acidity of the product and the acid amount thereof. Instead, a $NH_3$ adsorption method is used, where the physically adsorbed $NH_3$ by the product is desorbed at 200° C., and the acid amount is obtained by measuring the weight difference between the product before and after adsorption. The results are shown in Table 5. The amount of $NH_3$ adsorbed by the product is directly proportional to the sulfur content and is not proportional to the surface area of the product. From the data of surface analysis and elemental analysis, it is known that the product may has a high content of sulfophenylphosphonate group and a low surface area at the same time. So, one can infer that $NH_3$ molecules can penetrate into the layered product having a low surface area, and are adsorbed by the acidic —$SO_3H$ sites thereof. Since the size of $NH_3$ molecule is about the same as that of $N_2$, the penetration of $NH_3$ molecules into the layered product is driven mostly by the strong amine affinity of —$SO_3H$ functional group.

TABLE 5

| Precipitate | N, $10^{-4}$ mole/g | S, $10^{-4}$ mole/g |
| --- | --- | --- |
| Zr (6,0) | 20.3 | 20.5 |
| Zr (6,2) | 8.6 | 9.0 |
| Zr (6,4) | 3.6 | 3.9 |
| Zr (8,0) | 19.5 | 19.3 |
| Zr (8,2) | 10.5 | 9.7 |
| Zr (8,4) | 5.2 | 5.8 |
| Zr (10,0) | 17.1 | 20.1 |
| Zr (10,1) | 16.6 | 15.3 |
| Zr (10,2) | 10.4 | 9.3 |
| Zr (10,4) | 4.5 | 5.1 |
| Zr (20,0) | 12.5 | 12.4 |
| Zr (20,1) | 9.2 | 9.2 |
| Zr (20,5) | 3.5 | 3.6 |
| Zr (30.0) | 10.6 | 10.5 |

N: The values of the $NH_3$ adsorption in 200° C.
S: The values form the element analysis 6. The catalytic activity in MTBE synthesis reaction:

The reaction was carried out in an ordinary plug-flow reactor at atmospheric pressure. The catalyst, 0.2 g in powder form, was packed into a stainless steel reactor. A thermocouple well was fixed at the center of the catalyst bed to register the temperature in the reaction zone. Catalysts were preheated at 180° C. under $N_2$ flux for ca. 4 h, then cooled to reaction temperature, which was 80° C. if not specified. Methanol was introduced with a syringe pump (Sage 341 ) and the flow-rate of isobutene gas was controlled by a Brooks mass flow-meter. The flow-rates of methanol and isobutene were kept at 0.77 and 2.02 mL/min, respectively. The mixed reactants were preheated at the reaction temperature before entering the catalyst bed. The products were analyzed with a Hewlett-Packard 5890A gas chromatograph and a porapak S column was used to separate the product mixture.

6-1 ) Segregated products used as catalysts in MTBE synthesis reaction:

Table 6 shows the catalytic activities and selectivities of the products of 22Å interlayer spacing together with the commercially available A-15 catalyst in the MTBE synthesis reaction. Table 6 also shows the amount of —$SO_3H$ acid functional groupsand the surface areas of the products. it can be seen from Table 6 that the selectivities of MTBE are all high, >99.85%, and the conversions of isobutene vary significantly, in which Zr(20,0)-L has the highest isobutene conversion. Zr(20,0), Zr(30,0) and Zr(40,0) also have high isobutene conversions, about 70%, which are higher than that of the commercially available A-15 catalyst. The order of the acid amounts of these three product is Zr(20,0)>Zr(30, 0)>Zr(40,0), but the order of the surface areas is Zr(20, 0)<Zr(30,0)<Zr(40,0), as a result the isobutene conversions thereof are very close. From the data of Table 6, it is known that the products synthesized with molar ratios of $H_3PO_3$/ $HPO_3C_6H_4SO_3H$ ranging from 2 to 4 have higher catalytic activity. Moreover, the data in Table 1 indicate that this type of catalysts can be synthesized with a product yield above 55–66%. Consequently, they possess a great potential in industrial applications.

Figure 10:
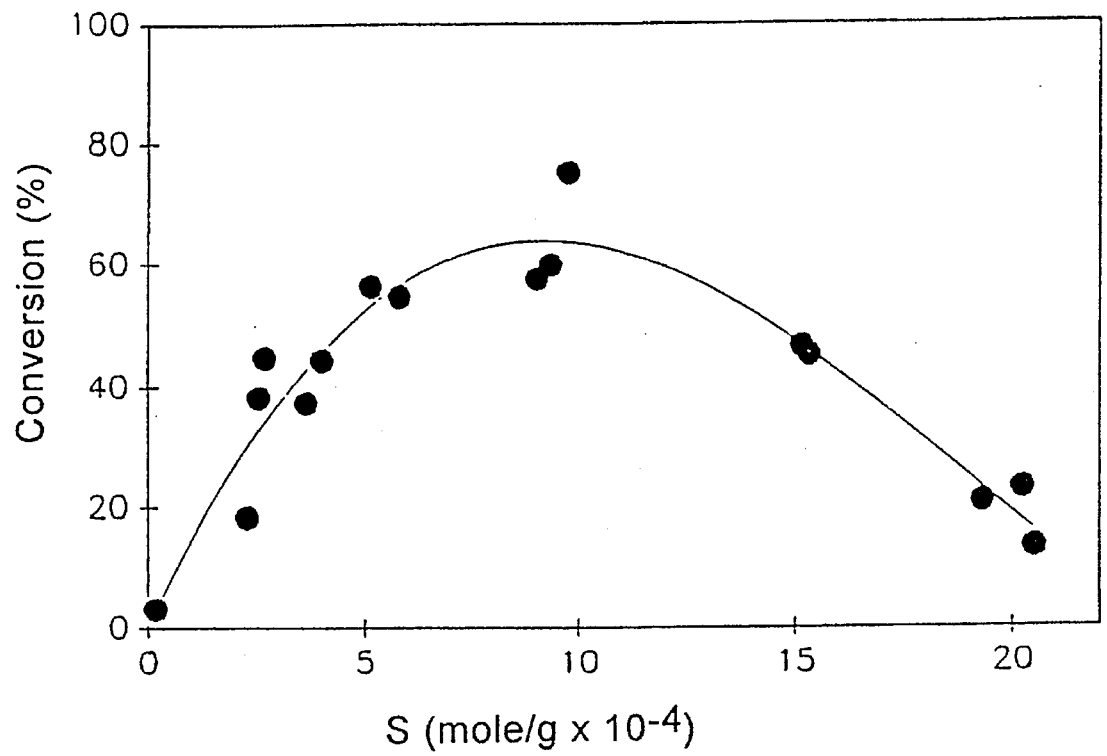
FIG. 10 is a plot which shows the variation of isobutene conversion as a function of the acid amount on the catalysts in the MTBE synthesis reaction of isobutene and methanol.
Figure 11:
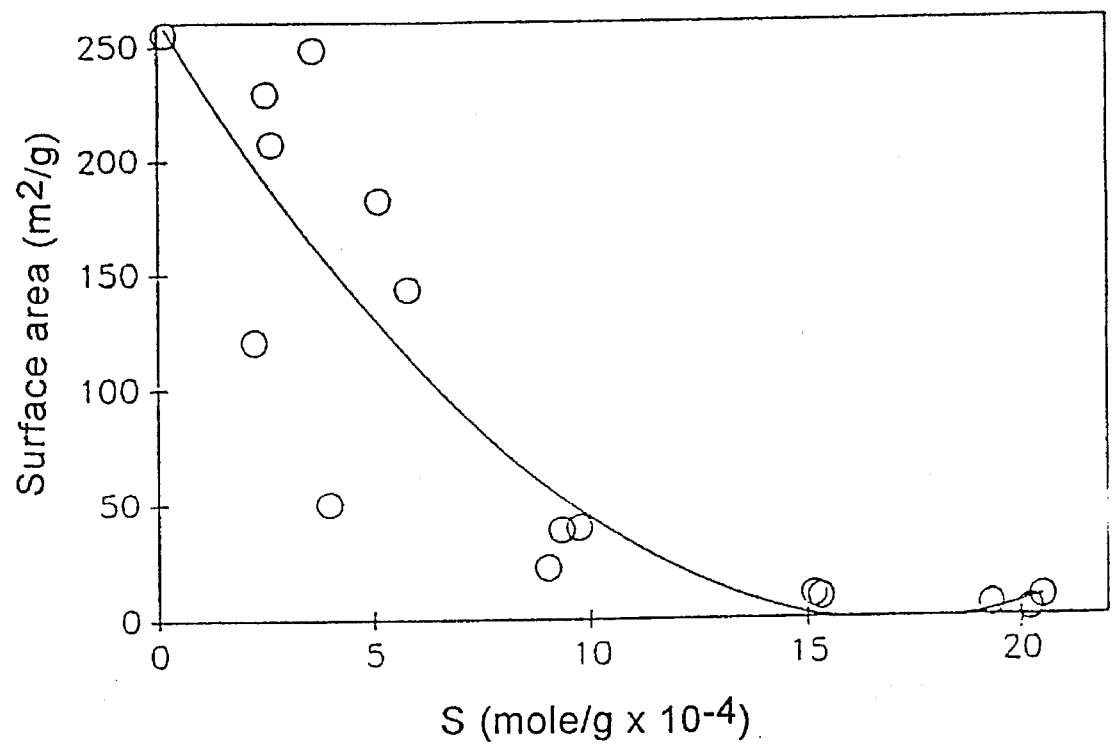
FIG. 11 is a plot which shows the variation of surface area as a function of the acid amount on the zirconium phosphite sulfophenylphosphonate catalysts.

6-2) products with d-spacing values about 16Å used as catalysts in MTBE synthesis reaction:

Table 7 shows the results of MTBE synthesis reaction wherein the products with a d-spacing value about 16Å are used as catalysts. Zr(8,2) has the highest catalytic activity in Table 7 and a high MTBE selectivity, >99.9%, close to that of the products with 21 d-spacing. FIGS. 10 and 11 show the isobutene conversion as a function of the acid amount and a function of surface area of the catalysts, respectively. The volcano relationship in FIG. 10 shows that the greatest activity is not obtained over the catalyst with the largest amount of acid sites. That, however, can be accounted for by the concomitant decrease of the surface as the acid amount is increased (FIG. 11). Among the catalysts in Table 7, Zr(8,2) has an isobutene conversion 8% higher than that of the commercially available A-15 catalyst, and it also possesses a great potential in industrial applications.

to avoid condensation thereof. The liquid products were collected by condensation at room temperature. The gas products were analyzed with a Hewlett-Packard 5890A gas chromatograph. The results show that the methanol conversion is about 15%, and the reaction products contain about 92% of dimethylether and 8% of hydrocarbons having a composition as follows:

| Composition of hydrocarbons, wt % | | | | | | | | | | |
|---|---|---|---|---|---|---|---|---|---|---|
| C1 | C2 | C2= | C3 | C3= | C4 | C5 | C6 | C7 | C8+ | aromatics |
| 1.2 | 0.2 | 16. | 0 | 28. | 20. | 15. | 6.5 | 4.6 | 0.4 | 8.1 |

TABLE 6

| Catalysts | Conversion[a] (%) | Selectivity[b] (%) | DME Yield[c] (× $10^{-4}$) | BET S. A. ($m^2/g$) | —$SO_3H$[d] × $10^{-4}$ mole/g |
|---|---|---|---|---|---|
| Zr (20,0) | 72.1 | 99.92 | 12.75 | 152 | 12.43 |
| Zr (30,0) | 73.0 | 99.95 | 12.18 | 162 | 10.50 |
| Zr (40,0) | 74.6 | 99.98 | 6.76 | 180 | 9.80 |
| zr (50,0) | 41.5 | 99.93 | 22.51 | 143 | 10.01 |
| Zr (20,1) | 35.7 | 99.91 | 19.31 | 125 | 9.25 |
| Zr (40,1) | 54.0 | 99.85 | 9.47 | 160 | 9.12 |
| Zr (20,0)-L | 79.4 | 99.95 | 9.16 | 188 | 13.26 |
| A-15 | 67.0 | 98.79 | 264 | — | — |

[a] isobutene conversion
[b] MTBE selectivity = MTBE conversion/isobutene conversion
[c] dimethyl ether yield based on methanol, $2CH_3OH \rightarrow CH_3$—O—$CH_3 + H_2O$
[d] sulfur content from elemental analysis

TABLE 7

| Catalysts | Conversion[a] (%) | Selectivity[b] (%) | DME Yield[c] (× $10^{-4}$) | BET S. A. ($m^2/g$) | —$SO_3H$[d] × $10^{-4}$ mole/g |
|---|---|---|---|---|---|
| Zr (6,0) | 13.5 | 99.99 | 19.78 | 8 | 20.49 |
| Zr (6,1) | 46.6 | 99.89 | 9.73 | 10 | 15.14 |
| Zr (6,2) | 57.4 | 99.97 | 6.10 | 22 | 9.02 |
| Zr (6,4) | 44.3 | 99.98 | 1.32 | 50 | 3.97 |
| Zr (6,7) | 18.3 | 99.99 | 1.31 | 120 | 2.26 |
| Zr (8,0) | 20.9 | 99.98 | 17.88 | 5 | 19.3 |
| Zr (8,2) | 75.1 | 99.98 | 4.53 | 39 | 9.74 |
| Zr (8,4) | 54.6 | 99.92 | 1.31 | 143 | 5.80 |
| Zr (8,7) | 44.7 | 99.98 | 1.30 | 207 | 2.66 |
| Zr (10,0) | 23.0 | 99.97 | 18.27 | 3 | 20.19 |
| Zr (10,1) | 45.2 | 99.94 | 14.38 | 9 | 15.31 |
| Zr (10,2) | 59.6 | 99.91 | 6.04 | 38 | 9.35 |
| Zr (10,4) | 46.3 | 99.97 | 2.10 | 182 | 5.12 |
| Zr (10,7) | 38.2 | 99.97 | 1.51 | 229 | 2.53 |
| Zr (20,5) | 37.4 | 99.99 | 0.85 | 248 | 3.61 |
| Zr (20,10) | 3.1 | 99.95 | 0.01 | 255 | 1.53 |

[a], [b], [c], [d] have definitions same as those in above Table 6

7. The catalytic activity in the methanol decomposition reaction:

The reaction was carried out in an ordinary plug-flow reactor at atmospheric pressure. The catalyst, 0.2 g in powder form, was packed into a stainless steel reactor of ⅜" diameter. A thermocouple well was fixed at the center of the catalyst bed to register the temperature in the reaction zone. Catalysts were preheated at 260° C. under $N_2$ flux for several hours, then cooled to the reaction temperature, 240° C. Methanol was introduced with a syringe pump (Sage 341) and the flow-rates of methanol was kept at 2.02 mL/min. The tube via which the reaction mixture exiting from the reactor was heated to a temperature of 100°–140° C. by heating pads The catalyst Zr(8,2) is a strong acid catalyst in view of the fact that a conversion of methanol to hydrocarbons and dimethyl ether is effectively carried out at a relatively low temperature of 240° C.

8. The catalytic activity in isobutene alkylation reaction:

Two types of reaction systems were used in this reaction. The first one is a plu-flow microreactor similar to the reaction system used in the 7. reaction except that the reaction temperature was 170° C., Zr(6,4) was the catalyst and the feed was 0.77 mL/min isobutene. The reaction products were analyzed with a Hewlett-Packard 5890A gas chromatograph. The results show that the isobutene conversion is about 5% and the reaction products contain about 91% of octene.

The second reaction system was a 100 mL fixed bed reactor, into which 0.2 g Zr(6,4) catalyst was charged. Isobutene having a pressure of two atms was introduce into the reactor, and reacted at room temperature for one hour. The analysis results show that almost all the isobutene is converted to octene, which indicates that this catalyst is a strong acid catalyst.

It can be seen from the results of the above reactions that the compound synthesized by the present invention is a strong acid catalyst suitable for using in a catalytic reaction taking place at temperatures lower than 290° C.

What is claimed is:

1. A method of preparing a zirconium phosphite sulfophenylphosphonates having the following formula $$Zr(HPO_3)_m(HPO_4)_n(PO_3C_6H_5)_y(PO_3C_6H_4SO_3H)_z$$

wherein m+n=x; x+y+z=2; 0.4≦x≦1.7; 0≦y≦1.6; and 0.01≦z0.8, the method comprising the following steps:

(a) reacting phenylphosphonic acid with an excess amount of fuming sulfuric acid at a temperature from about 80° C. to about 150° C. to convert substantially all the phenylphosphonic acid to sulfophenylphosphonic acid;

(b) cooling the reaction mixture to a temperature below about 80° C.;

(c) mixing the cooled reaction mixture with: (i) phosphorous acid; (ii) an aqueous or organic solution of zirconium salt; and (iii) phenylphosphonic acid when y is >0, to give a resultant solution mixture;

(d) stirring the resultant solution mixture at a temperature between about 150° C. and room temperature until a co-precipitate is formed therein;

(e) removing the co-precipitate from the solution mixture; and (f) washing and drying the co-precipitate.

2. The method according to claim 1, wherein the mixing molar ratio of zirconium (Zr): sulfophenylphosphonic acid ($H_2PO_3C_6H_4SO_3H$): phosphorous acid ($H_3PO_3$): phenylphosphonic acid ($H_2PO_3C_6H_5$) in step (c) is 1:10:a:b, wherein 6≦a≦50; 0≦b≦10.

3. The method according to claim 1, wherein the reaction temperature in step (a) is about 120° C.

4. The method according to claim 1, wherein the stirring temperature in step (c) is about 110° C.

5. The method according to claim 1, wherein the cooling temperature in step (b) is room temperature.

6. The method according to claim 1, wherein the aqueous or organic solution of zirconium salt is an aqueous solution of $ZrOCl_2 \cdot 8H_2O$.

7. The method according to claim 1, wherein said phosphorous acid and said phenylphosphonic acid in step (c) are mixed with said cooled reaction mixture in the form of an aqueous solution.

8. A solid acid catalyst for use in an acid catalyzed reaction comprising a zirconium phosphite sulfophenylphosphonate prepared by the method of claim 1, said solid acid catalyst having inteflayer spacing of from 18Å to 30Å.

9. The solid acid catalyst according to claim 8, wherein said acid catalyzed reaction is gas phase synthesis of methyl tert-butyl ether (MTBE) from methanol and isobutene.

10. A compound prepared according to the method of claim 1, said compound having interlayer spacing of from 18Å to 30Å.

* * * * *